US012611143B2

(12) United States Patent
Saeki

(10) Patent No.: US 12,611,143 B2
(45) Date of Patent: Apr. 28, 2026

(54) ASSIST TOOL AND SENSOR KIT

(71) Applicant: NIHON KOHDEN CORPORATION, Tokyo (JP)

(72) Inventor: Kota Saeki, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 18/933,426

(22) Filed: Oct. 31, 2024

(65) Prior Publication Data

US 2025/0152099 A1 May 15, 2025

(30) Foreign Application Priority Data

Nov. 9, 2023 (JP) ................................. 2023-191461

(51) Int. Cl.
*A61B 5/00* (2006.01)
*A61B 5/024* (2006.01)
*A61B 5/1455* (2006.01)
(52) U.S. Cl.
CPC ........ *A61B 5/6826* (2013.01); *A61B 5/02438* (2013.01); *A61B 5/14552* (2013.01); *A61B 5/6831* (2013.01)

(58) Field of Classification Search
CPC ............ A61B 5/02438; A61B 5/14552; A61B 5/6826; A61B 5/6831; A61B 5/6838
See application file for complete search history.

(56) References Cited

U.S. PATENT DOCUMENTS

2017/0014075 A1    1/2017   Morimura et al.
2019/0298239 A1    10/2019  Saeki et al.

FOREIGN PATENT DOCUMENTS

JP          6554459 B2      7/2019
JP          7066485 B2      5/2022

*Primary Examiner* — Mark D Remaly
(74) *Attorney, Agent, or Firm* — Sughrue Mion, PLLC

(57) ABSTRACT

An assist tool to be attached to a finger of a subject. The assist tool includes a support body placed on a first side of the finger in a case where the support body is attached to the finger, a bag body configured to be placed on a second side, the second side being opposite to the first side of the finger with respect to the finger, and a fluid passage communicating with inside of the bag body. A physiological information detector for obtaining the physiological information is configured to be placed between the finger and the support body, and between the finger and the bag body. A spacer is provided in the support body such that the finger does not enter a fingertip side of the bag body.

6 Claims, 6 Drawing Sheets

ASSIST TOOL AND SENSOR KIT

CROSS-REFERENCE TO RELATED APPLICATIONS

This application is based on and claims priority under 35 USC 119 from Japanese Patent Application No. 2023-191461 filed on Nov. 9, 2023, the entire content of which is incorporated herein by reference.

TECHNICAL FIELD

The presently disclosed subject matter relates to an assist tool to be attached to a finger of a subject and assist in obtaining physiological information on the subject by a sensor. The presently disclosed subject matter further relates to a sensor kit that obtains physiological information on a subject using the assist tool.

BACKGROUND ART

An example of obtaining physiological information includes measurement of capillary refill time. The capillary refill time is a simple indicator for assessing presence and absence of shock, and is a technique widely used in an emergency medical field such as determination of necessity of fluid and triage (priority evaluation in mass casualty situations). Specifically, a medical worker presses on a biological tissue such as a fingertip of a subject, and visually checks a color change in a nail and skin after releasing the pressure. If the color returns to normal within substantially two seconds, the subject is considered to be under a normal condition. Since this method involves manually pressing on the biological tissue and visually checking the color change of the skin, it lacks quantitativeness and is prone to measurement errors by an examiner.

Accordingly, JP6554459B specifies capillary refill time of a subject with a physiological information obtaining system using a sensor. In the physiological information obtaining system of JP6554459B, the sensor is attached to a finger of the subject by an assist tool, and physiological information is obtained from the sensor by changing pressure applied to the finger by a bag body of the assist tool. An assist tool of JP7066485B includes a support body and a bag body. A first side of a finger of a subject is placed on the support body. In this state, the bag body is placed on a second side of the finger by bending a hinge. At this time, a light emitter is placed on one of a pad side and a nail side, and a light detector is placed on the other side. Capillary refill time is specified from a change in a detected light intensity of the light detector when pressure by the bag body is released.

To press the finger of the subject, the tool is desirably attached such that a center of the bag body is aligned with a center of a nail of the finger on which the light emitter and the light detector of the sensor are placed. However, since a finger tip of the subject is in a vicinity of the hinge, the nail center may remarkably deviate from the center of the bag body depending on a size of the finger, and pressing by the bag body may be difficult.

SUMMARY OF INVENTION

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an assist tool to be attached to a finger of a subject, the assist tool assisting in obtaining physiological information on the subject, the assist tool including:

a support body placed on a first side of the finger in a case where the support body is attached to the finger;

a bag body configured to be placed on a second side, the second side being opposite to the first side of the finger with respect to the finger; and a fluid passage communicating with inside of the bag body, in which the first side is one of a pad side of the finger and a nail side of the finger, the second side is an other one of the pad side of the finger and the nail side of the finger, a physiological information detector for obtaining the physiological information is configured to be placed between the finger and the support body, and between the finger and the bag body, and a spacer is provided in the support body such that the finger does not enter a fingertip side of the bag body.

According to an aspect of the present disclosure, there is provided a sensor kit including:

a sensor tool including a physiological information detector for obtaining physiological information on a subject; and an assist tool configured to be attached to a finger of the subject to accommodate the physiological information detector and configured to assist in obtaining the physiological information on the subject by the sensor tool, in which the assist tool includes:

a support body configured to be placed on a first side of the finger in a case where the support body is attached to the finger;

a bag body configured to be placed on a second side, the second side being opposite to the first side of the finger with respect to the finger; and a fluid passage communicating with inside of the bag body, the first side is one of a pad side of the finger and a nail side of the finger, the second side is an other one of the pad side of the finger and the nail side of the finger, the physiological information detector is configured to be placed between the finger and the support body, and between the finger and the bag body, and the support body is provided with a spacer such that the finger does not enter a fingertip side of the bag body.

BRIEF DESCRIPTION OF DRAWINGS

Exemplary embodiment(s) of the present invention will be described in detail based on the following figures, wherein.

DESCRIPTION OF EMBODIMENTS

Assist Tool in Related Art

Figure 1:
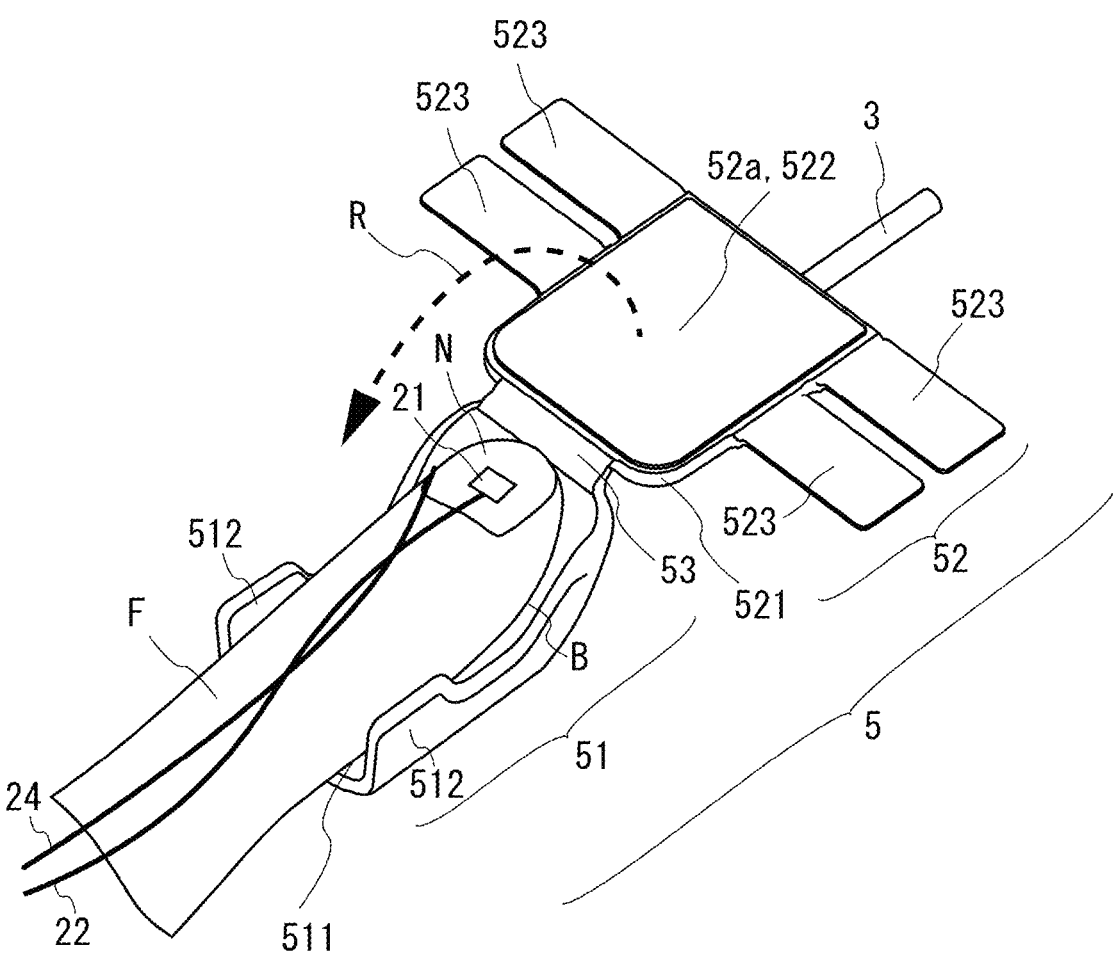
FIG. 1 is a perspective view illustrating a state in which a finger is inserted into an assist tool in the related art.

FIG. 1 is a perspective view illustrating a state in which a finger F is inserted into an assist tool 5 in the related art. A physiological information detector for obtaining physiological information on a subject is attached to the finger F. The physiological information detector of this example is a so-called pulse photometer probe, and includes a light emitter 21 and a light detector 23. In FIG. 1, the light emitter 21 is attached to a nail N, and the light detector 23 is hidden under the finger F. A sensor tool 2 can include the light emitter 21, a wire 22 connected to the light emitter 21, the light detector 23, and a wire 24 connected to the light detector 23. The light emitter 21 is an LED attached to the nail N. The light detector 23 hidden by the finger F is attached to a pad B side. The light emitter 21 is configured to emit light toward the light detector 23. The transmitted light is detected by the light detector 23 and a light detection signal is sent to the wire 24. The sensor tool 2 is attached by taping a tape (not illustrated) around the finger F.

The assist tool 5 is attached to the finger F of the subject, changes pressure to the finger F, and assists in obtaining the physiological information on the subject from the sensor tool 2. The assist tool 5 can include a support body 51, a lid body 52, and a hinge 53 connecting the support body 51 and the lid body 52. The assist tool 5 in FIG. 1 is in a state where the lid body 52 is open and the finger F is before being pressed in the support body 51. In the support body 51, side walls 512 rises from two sides of a bottom wall 511, and the finger F is accommodated between the side walls 512 with the pad B side attached to the bottom wall 511 via a tape (not illustrated).

The lid body 52 is provided with a lid body base 521, a bag film 522, and belts 523. Two belts 523 extend laterally from each of two sides of the lid body base 521. A part of the lid body base 521 and the bag film 522 constitute a bag body 52a. Inside of the bag body 52a communicates with inside of a tube 3. In the assist tool 5, in a case where the hinge 53 is bent and the lid body 52 is covered on the support body 51, the physiological information detector that is a sensor for obtaining physiological information is placed between the finger F and the support body 51 and between the finger F and the bag body 52a.

Figure 2:
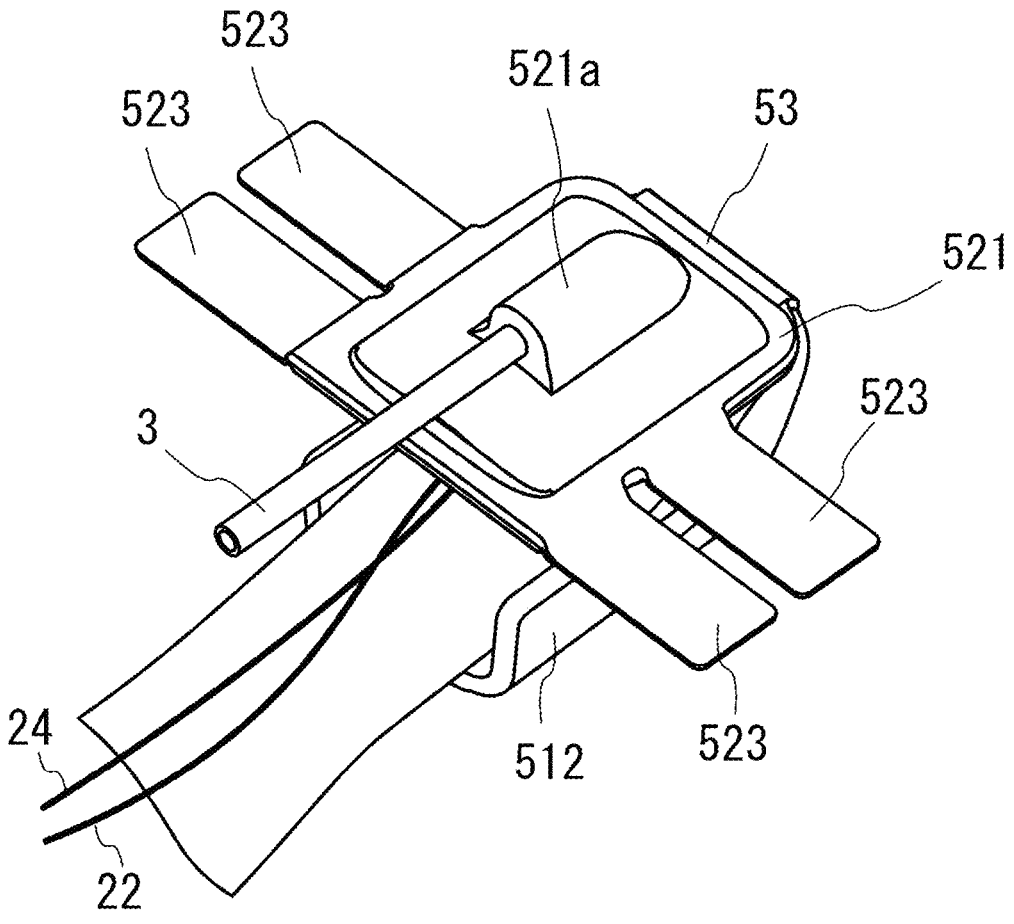
FIG. 2 is a perspective view illustrating a state in which the finger is inserted into the assist tool in the related art and a lid body is closed.

FIG. 2 illustrates a state where the lid body 52 in FIG. 1 is rotated as indicated by a dotted arrow R by the bending of the hinge 53 and covered on the support body 51. A part of the lid body base 521 projects and forms a fluid passage 521a inside. The tube 3 configured to supply compressed air is connected to the fluid passage 521a. A surface fastener (not illustrated) is provided on lower surfaces of the four belts 523 and an outer surface of the support body 51. In a case where the belts 523 are wrapped around the outer surface of the support body 51 from the state illustrated in FIG. 2 and the lid body 52 is fixed to the support body 51, the finger F can be fixed inside the assist tool 5.

Figure 3:
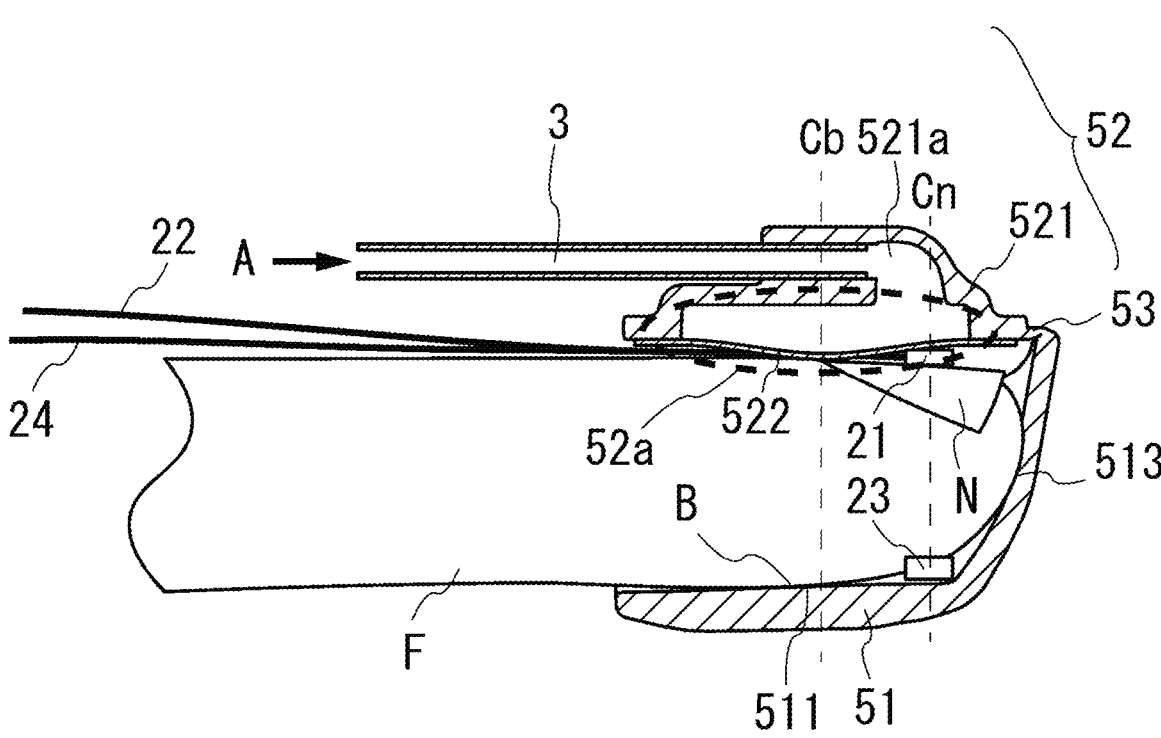
FIG. 3 is a sectional view illustrating a state in which the finger is inserted into the assist tool in the related art and the lid body is closed.

FIG. 3 is a sectional view of a state where the finger F is inserted into the assist tool 5 in the related art and the lid body 52 is closed. In FIG. 3, the assist tool 5 is illustrated in section, and the finger F and the sensor tool 2 such as the light emitter 21 are illustrated in side surfaces. The light emitter 21 is attached to the nail N of the finger F by taping, and the light detector 23 is attached to the pad B side by taping. Also in FIG. 3, a tape that taped peripheries of the finger F and the sensor tool 2 is not illustrated. Although not illustrated, in the state of FIG. 3, the belts 523 are wrapped around the outer surface of the support body 51, and the lid body 52 is fixed to the support body 51 by a surface fastener (not illustrated).

In FIG. 3, the hinge 53 is bent and the lid body 52 is covered on the finger F. In the lid body 52, the bag film 522 is bonded to a periphery of a lower surface of the lid body base 521 and forms the bag body 52a as illustrated by a dotted ellipse. The fluid passage 521a formed in the upper portion of the lid body base 521 communicates with the inside of the bag body 52a, and an opposite side communicates with the inside of the tube 3. In the finger F located under the bag body 52a, a pad B is in contact with the bottom wall 511 of the support body 51, and a tip end of the finger F reaches a rising portion 513 of the support body 51. An upper end of the rising portion 513 rises on a tip end side of the finger F is connected to the hinge 53.

As indicated by an arrow A, compressed air is supplied from the tube 3 to the bag body 52a in FIG. 3, and the bag film 522 bulges downward. However, a bag body center line Cb, which is a center line of the bag body 52a, does not pass through the nail N, a nail center line Cn largely deviates from the bag body center line Cb, and the light emitter 21 placed on the nail N and the light detector 23 located below the light emitter 21 largely deviate from the bag body center line Cb. In this state, pressure by the bag body 52a is less likely to act on the nail N, and it is difficult to measure capillary refill time.

Assist Tool of Embodiment

Figure 4:
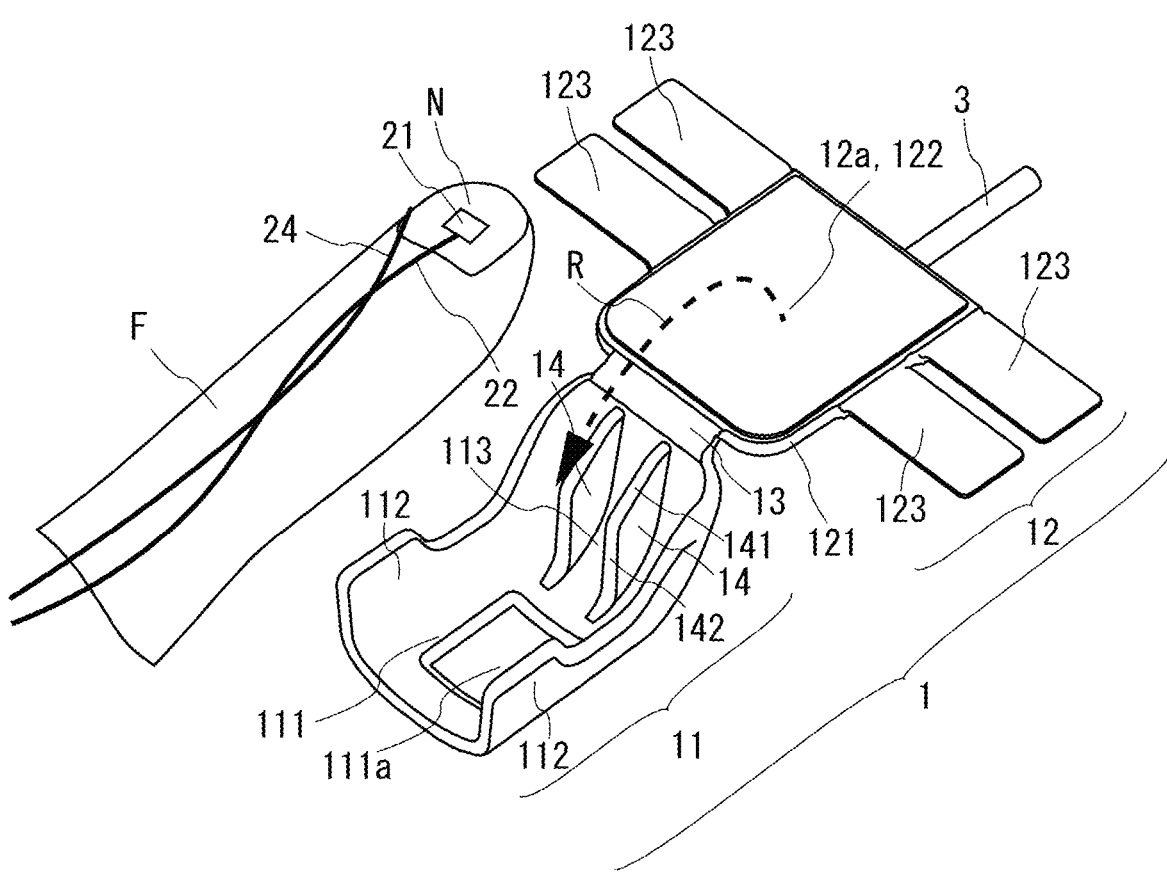
FIG. 4 is a perspective view illustrating a state before a finger is inserted into an assist tool according to an embodiment of the presently disclosed subject matter.

FIG. 4 is a perspective view illustrating a state before the finger F is inserted into an assist tool 1 according to the embodiment of the presently disclosed subject matter. A physiological information detector for obtaining physiological information on a subject is attached to the finger F. The physiological information detector according to the present embodiment is a so-called pulse photometer probe, and includes the light emitter 21 and the light detector 23. In FIG. 4, the light emitter 21 is attached to the nail N, and the light detector 23 is hidden under the finger F. The sensor tool 2 can include the light emitter 21, the wire 22 connected to the light emitter 21, the light detector 23, and the wire 24 connected to the light detector 23. The light emitter 21 is an LED attached to the nail N. The light detector 23 hidden by the finger F is attached to a pad B side. The light emitter 21 is configured to emit light toward the light detector 23. The transmitted light is detected by the light detector 23 and a light detection signal is sent to the wire 24. The sensor tool 2 is attached by taping a tape (not illustrated) around the finger F.

The assist tool 1 is attached to the finger F of the subject, is configured to change pressure to the finger F, and is configured to assist in obtaining the physiological information on the subject from the sensor tool 2. The assist tool 1 can include a support body 11, a lid body 12, and a hinge 13 connecting the support body 11 and the lid body 12. The assist tool 1 in FIG. 4 is in a state in which the lid body 12 is open, and the finger F is before being pressed in the support body 11. In the support body 11, side walls 112 rises from two sides of a bottom wall 111, and the finger F is accommodated between the side walls 112, the pad B side is attached to the bottom wall 111 via a tape (not illustrated). The sensor tool 2 and the assist tool 1 used here are combined and sold and distributed as a sensor kit.

The lid body 12 is provided with a lid body base 121, a bag film 122, and belts 123. Two belts 123 extend laterally from each of two sides of the lid body base 121. A part of the lid body base 121 and the bag film 122 form a bag body 12a. Inside of the bag body 12a communicates with inside of the tube 3. In the assist tool 1, in a case where the hinge 13 is bent and the lid body 12 is covered on the support body 11, the physiological information detector that is a sensor for obtaining physiological information is placed between the finger F and the support body 11 and between the finger F and the bag body 12a. An upper end of a rising portion 113 rises on a tip end side of the finger F is connected to the hinge 13.

Unlike the example in the related art, the support body 11 of the assist tool 1 according to the embodiment can include spacers 14 at the rising portion 113 on a fingertip side. The spacers 14 are provided in two positions on the fingertip side of the support body 11. Each of the spacers 14 has a thin plate shape. Each of the spacers 14 can include an inclining upper surface 141 gradually descending from a position in a vicinity of the hinge 13 of the rising portion 113, and a stopper surface 142 extending further rapidly. A concave portion 111a is provided in the bottom wall 111.

Figure 5:
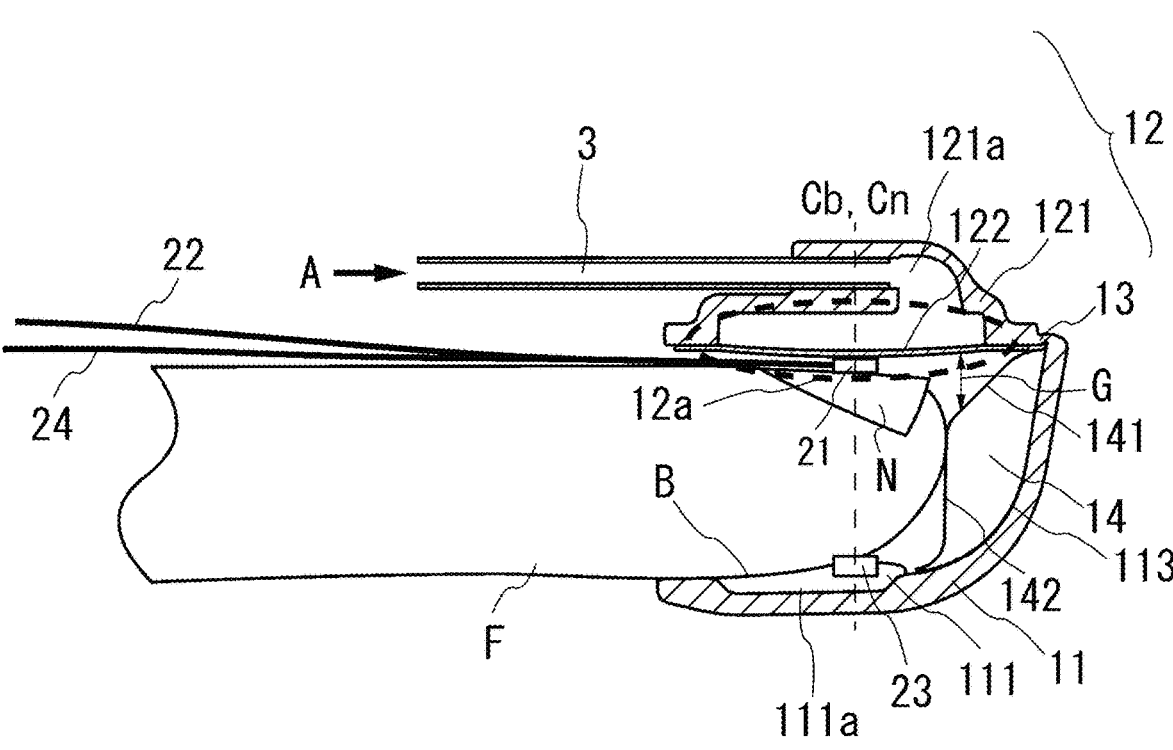
FIG. 5 is a sectional view illustrating a state in which the finger is inserted into the assist tool according to the embodiment of the presently disclosed subject matter and a lid body is closed.

FIG. 5 is a sectional view illustrating a state where the finger F is inserted into the assist tool 1 according to the embodiment of the presently disclosed subject matter and the lid body 12 is closed as indicated by the dotted arrow R in FIG. 4. In FIG. 5, the assist tool 1 is illustrated in section. The light emitter 21 is attached to the nail N of the finger F by taping, and the light detector 23 is attached to the pad B side by taping. Also in FIG. 5, a tape that taped peripheries of the finger F and the sensor tool 2 is not illustrated. In the state of FIG. 5, the belts 123 are wrapped around an outer surface of the support body 11 as in the example in the related art, and the lid body 12 is fixed to the support body 11 by a surface fastener (not illustrated).

In FIG. 5, the hinge 13 is bent and the lid body 12 is covered on the finger F. In the lid body 12, the bag film 122 is bonded to a periphery of a lower surface of the lid body base 121 and forms the bag body 12a as illustrated by a dotted ellipse. A fluid passage 121a formed in an upper portion of the lid body base 121 communicates with the inside of the bag body 12a, and an opposite side communicates with the inside of the tube 3. The pad B of the finger F located under the bag body 12a is in contact with the bottom wall 111 of the support body 11. The support body 11 of the assist tool 1 is provided with the spacers 14 such that the finger F does not enter a hinge 13 side on the fingertip side of the bag body 12a. A tip end of the finger F reaches the stopper surfaces 142 of the spacers 14. The light detector 23 is fitted into the concave portion 111a provided in the bottom wall 111. Since the concave portion 111a is provided, the finger F is pressed from above and the pad B is fitted into the concave portion 111a and is less likely to be removed from the assist tool 1.

Figure 6:
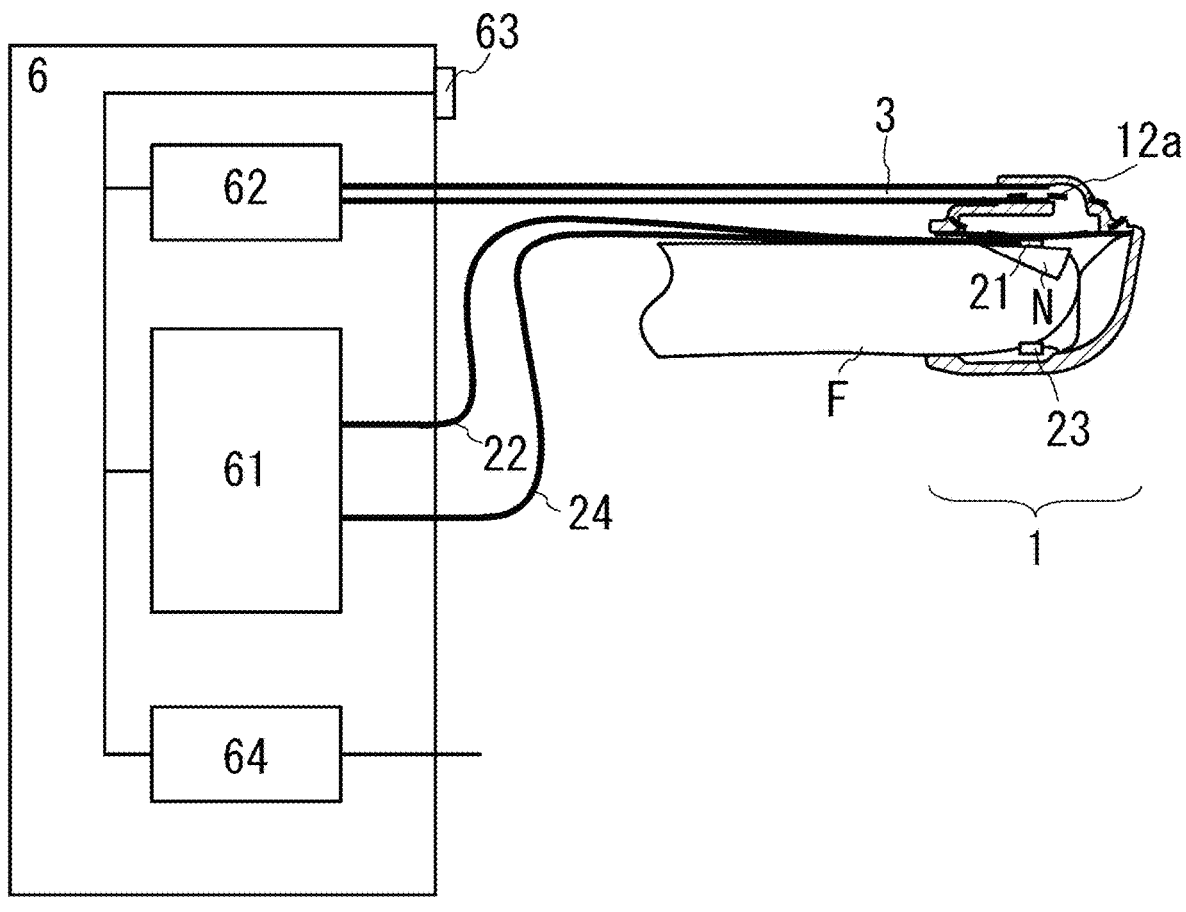
FIG. 6 illustrates a situation of obtaining physiological information using the assist tool according to the embodiment of the presently disclosed subject matter.

In this manner, in a state where the sensor tool 2 and the assist tool 1 are attached to the finger F, physiological information is obtained by a physiological information obtaining device 6. FIG. 6 illustrates a situation of obtaining physiological information using the assist tool 1 of the embodiment. The assist tool 1, the light emitter 21, the wire 22, the light detector 23, the sensor tool 2 with the wire 24, and the tube 3 are illustrated in FIG. 5. The tube 3 and the wires 22 and 24 are connected to the physiological information obtaining device 6. The physiological information obtaining device 6 can include an information obtaining unit 61, a pressure adjustment unit 62, a switch 63, and an information output unit 64. The information obtaining unit 61, the pressure adjustment unit 62, the switch 63, and the information output unit 64 are connected to each other inside the physiological information obtaining device 6.

The wires 22 and 24 are connected to the information obtaining unit 61, and the light emitter 21 emits light and a detected light amount of the light detector 23 is obtained. This makes it possible to calculate capillary refill time. Since the sensor tool 2 functions as a probe of a pulse oximeter, the information obtaining unit 61 can obtain other physiological information such as non-invasive arterial blood oxygen saturation (SpO2).

The tube 3 is connected to the pressure adjustment unit 62, and compressed air is supplied into and removed from the tube 3 by opening an air valve (not illustrated). The switch 63 is used to start obtaining the physiological information, and the information output unit 64 outputs the physiological information obtained by the physiological information obtaining device 6 to outside as information data, display information, and audio information.

In FIG. 6, when the switch 63 is pressed and turned ON, compressed air is supplied from the pressure adjustment unit 62 to the tube 3. The supplied compressed air inflates the bag body 12a of the assist tool 1 and presses the nail N of the finger F. Accordingly, blood is pushed out from a capillary in a vicinity of the nail N. Light transmitted from the light emitter 21 is detected by the light detector 23 without much absorption of light by the blood.

When prescribed time elapses, the pressure adjustment unit 62 stops supplying compressed air and removes the compressed air to reduce the pressure. At this time, the nail N is released from being pressed by the bag body 12a of the assist tool 1. Then, the blood returns to or does not return to the capillary in the vicinity of the nail N depending on a state of the subject. Light transmitted from the light emitter 21 is detected by the light detector 23 with a changed light absorption depending on a degree of return of the blood. The information obtaining unit 61 measures the capillary refill time based on a change in the detected light amount after the pressure adjustment unit 62 reduces the pressure. The information obtaining unit 61 can further obtain other physiological information such as non-invasive arterial blood oxygen saturation (SpO2) when no pressure is generated by the pressure adjustment unit 62.

The capillary refill time and other physiological information measured by the information obtaining unit 61 are output from the information output unit 64. This output can be performed in a form of information data, display information, audio information, and the like.

In the present embodiment in FIG. 5, the support body 11 of the assist tool 1 is provided with the spacers 14 so that the finger F does not enter the hinge 13 side on the fingertip side of the bag body 12a. The tip end of the finger F reaches the stopper surfaces 142 of the spacers 14. Since the tip end of the finger F is pressed by the stopper surfaces 142 of the spacers 14, a position of the nail N is separated from an end portion of the bag body 12a located in a vicinity of the hinge 13. A center of the nail N substantially passes through the bag body center line Cb. The nail center line Cn is perpendicular to an extending direction of the finger F from the center of the nail N to the pad B side. The light emitter 21 and the light detector 23 are provided substantially in a position of the nail center line Cn. In FIG. 5, the bag body center line Cb coincides with the nail center line Cn, and the bag body center line Cb passes through the light emitter 21 and the light detector 23.

As described above, since the spacers 14 are provided, the position of the finger F retreats from a vicinity of the fingertip side of the bag body 12a, and center positions of the nail N and the bag body 12a are easily aligned. Accordingly, stable refill time measurement can be implemented by effective pressing and release of pressing. The number of the spacers 14 may be one, and when there are two spacers as in the embodiment, the spacers 14 abut against the tip end of the finger F in two positions when being attached to the finger F with improved stability and attachment comfort.

As indicated by the arrow A, compressed air is supplied from the tube 3 to the bag body 12a of FIG. 5, and the bag film 122 bulges downward. The bag body center line Cb, which is the center line of the bag body 12a, passes through the nail N. In this state, pressing by the bag body 12a sufficiently acts on the nail N to discharge the blood of the capillary. For this reason, the capillary refill time can be measured favorably.

In the embodiment, a gap G is defined between a nail side of the spacers 14 and the bag body 12a as illustrated in FIG. 5 to avoid interference when the bag body 12a bulges downward. Upper surfaces of the spacers 14 are the inclining upper surfaces 141 and gradually descend toward the nail N from the hinge 13. The sufficient gap G is defined between the inclining upper surfaces 141 of the spacers 14 and the bag film 122 of the bag body 12a. For this reason, when the bag film 122 of the bag body 12a largely bulges downward, the bag film 122 can sufficiently press the nail N and the light emitter 21 without interfering with the spacers 14. Since the gap G due to the inclining upper surfaces 141 is defined, the finger F can be placed in an appropriate position of the assist tool 1 even for a subject having the long nail N.

As illustrated in FIG. 5, when the assist tool 1 is attached to the finger F of the subject, the support body 11 is placed on the pad side and the tip end side. The pad side is an example of a first side of the finger. The bag body 12a is placed on a nail side of the finger F. The nail side of the finger F is opposite to the pad side, and is an example of a second side of the finger. The nail side of the finger F may be the first side of the finger, and the pad side may be the second side. In either case, the support body 11 is placed on the first side of the finger F when being attached, and the bag body 12a is placed on the second side opposite to the first side with the finger F interposed in between.

In the above-described embodiment, each of the belts 123 can include a pair of belt-shaped members extending from two side portions of the bag body 12a. Alternatively, the belt 123 may be constituted by a single belt-shaped member extending from one side portion of the bag body 12a. In this case, the single belt-shaped member is wound from one side wall 112 to the other side wall 112 through the bottom wall 111.

In the above-described embodiment, the light emitter 21 and the light detector 23 are respectively placed on the nail side and the pad side. Alternatively, the light emitter 21 and the light detector 23 may be respectively placed on the pad side of the finger F and the nail side. Alternatively, the light emitter 21 and the light detector 23 may be both placed on one of the nail side of the finger F and the pad side. In this case, light reflected by the finger F can be detected to obtain physiological information such as the capillary refill time.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An assist tool to be attached to a finger of a subject, the assist tool assisting in obtaining physiological information on the subject, the assist tool comprising:
   a support body placed on a first side of the finger in a case where the support body is attached to the finger, the support body including a distal end toward which the finger is inserted and a proximal end;
   a bag body configured to be placed on a second side, the second side being opposite to the first side of the finger with respect to the finger; and
   a fluid passage communicating with inside of the bag body,
   wherein the first side is one of a pad side of the finger and a nail side of the finger,
   the second side is an other one of the pad side of the finger and the nail side of the finger,
   a physiological information detector for obtaining the physiological information is configured to be placed between the finger and the support body, and between the finger and the bag body, and
   a spacer is provided at the distal end of the support body and is configured to prevent the finger from entering a fingertip side of the bag body.

2. The assist tool according to claim 1,
   wherein the support body includes a rising portion on the distal end of the support body, and
   the spacer is fixed to the rising portion, on the distal end of the support body.

3. The assist tool according to claim 2,
   wherein a gap is defined between the second side of the spacer and the bag body to avoid interference in a case where the bag body is inflated.

4. The assist tool according to claim 3,
   wherein the bag body is provided in a lid body, and
   a fingertip side of the lid body and a fingertip side of the support body are connected by a hinge.

5. The assist tool according to claim 1,
   wherein the spacer is provided in two positions on a fingertip side of the support body.

6. A sensor kit comprising:
   a sensor tool including a physiological information detector for obtaining physiological information on a subject; and
   an assist tool configured to be attached to a finger of the subject to accommodate the physiological information detector and configured to assist in obtaining the physiological information on the subject by the sensor tool,
   wherein the assist tool includes:
   a support body configured to be placed on a first side of the finger in a case where the support body is attached to the finger, the support body including a distal end toward which the finger is inserted and a proximal end;

a bag body configured to be placed on a second side, the second side being opposite to the first side of the finger with respect to the finger; and a fluid passage communicating with inside of the bag body, the first side is one of a pad side of the finger and a nail side of the finger, the second side is an other one of the pad side of the finger and the nail side of the finger, the physiological information detector is configured to be placed between the finger and the support body, and between the finger and the bag body, and the support body is provided with a spacer at the distal end of support body and is configured to prevent the finger from entering a fingertip side of the bag body.

* * * * *